United States Patent [19]

Kaplan et al.

[11] Patent Number: 5,294,541
[45] Date of Patent: Mar. 15, 1994

[54] REAL-TIME MONITORING OF OXIDATIVE PRODUCTS FROM IN VITRO CELL-BIOMATERIAL INTERACTION USING CHEMILUMINESCENCE

[75] Inventors: David S. Kaplan, Fairfax, Va.; Grace L. Picciolo, Fort Washington; Edward P. Mueller, Bayridge, both of Md.

[73] Assignee: The United States of America as represented by the Secretary of the Department of Health and Human Services, Washington, D.C.

[21] Appl. No.: 912,590

[22] Filed: Jul. 13, 1992

Related U.S. Application Data

[63] Continuation of Ser. No. 410,626, Sep. 21, 1989, abandoned.

[51] Int. Cl.⁵ .......................... C12Q 1/02; C12Q 1/06
[52] U.S. Cl. ........................................ 435/29; 435/39
[58] Field of Search .................................. 435/29, 39

[56] References Cited

U.S. PATENT DOCUMENTS 4,788,142  11/1988  Hosaka et al. ..................... 435/29

OTHER PUBLICATIONS

Barth et al. (1988) Abstract Only J. Invest. Surg. 1(4) 291–297.

*Primary Examiner*—Christine M. Nucker
*Assistant Examiner*—D. R. Preston
*Attorney, Agent, or Firm*—Birch, Stewart, Kolasch & Birch

[57] ABSTRACT

A chemiluminescence method for continuously monitoring in real time the generation of oxidative products such as hydrogen peroxide and superoxide from in vitro cell-biomaterial interactions using cell lines such as Human Leukemic cells (HL-60); tumor cell line hybridomas; cells lacking the respiratory burst such as Chronic Granulomatous Disease cells as controls; Monocytic cell lines; Primary Human cells such as monocytes, pmns, fibroblasts, endothelial cells; and whole and isolated blood cells. The oxidative products have the potential for the degradation of the biomaterial and thus this information can be used to aid in predicting the functional lifetime of the biomaterial when it is used to fabricate an implanted medical device. Further, this method may be used to determine the amount of activation of biological cells which is inferred from the amount of oxidative products. This activation level aids in the determination of the degree of the inflammatory response and thus influences the degree of acceptance of the biomaterial. Thus, toxicity and biocompatability tests could be supported by these measurements.

21 Claims, 10 Drawing Sheets

REAL-TIME MONITORING OF OXIDATIVE PRODUCTS FROM IN VITRO CELL-BIOMATERIAL INTERACTION USING CHEMILUMINESCENCE

This application is a continuation of application Ser. No. 07/410,626 filed on Sep. 21, 1989, now abandoned.

BACKGROUND OF THE INVENTION

1. Field of the Invention

The present invention relates to a method for monitoring the generation of oxidative products from cell-biomaterial interactions. More specifically, the present invention relates to a chemiluminescence method for continuously monitoring in real time the generation of oxidative products from cell-biomaterial interactions in vitro.

2. Description of Related Art

With the improvements in health and increased life span in the United States population, comes the need for improved reliability of implanted medical devices, particularly those which are used for life-supporting structural and organ systems. Up to now, the expected life time for these devices was on the order of 10 years. As in the case of the prosthetic heart valves, pacemakers, orthopedic prostheses, etc., patient survival is extended for longer periods necessitating a corresponding improvement in reliable performance requirements (Kambic et al., "Biomaterials in artificial organs," *Chem. and Eng. News,* Apr. 14, pp. 31-49, 1986). In fact, the types of problems associated with long term usage are quite different from those of short term usage.

Performance parameters fall into two general categories: materials properties and dynamic function. Materials properties are tested by the classical methods of physico-chemical characterization and dynamic function is tested in simulated environments with accelerated life tests. The compatibility of the devices and their materials with the host, the human body, is tested with a classical battery of biocompatibility tests associated with the intended site of use (ASTM Standard 748-82, British Standards Institute No. 5736, and Canadian Standards Association CAN3-Z310.6-M84, September 1984; Williams, Definitions in Biomaterials, Proceedings of a consensus conference of the European Society for Biomaterials, Chester, UK, Mar. 3-5, 1986, Elsevier Press, 1988). These tests include acute and chronic toxicity determinations in experimental animals and mutagenic and carcinogenic tests in animals and tissue culture. Long term testing of any kind is expensive and often requires use of a variety of different animal models. Manufacturers will have their products or components tested by a battery of tests chosen according to selected criteria (North American Science Associates, Incorporated (NAmSA) Safety Evaluation Guidelines, 1989).

The data required to document extended usage in the human are either extrapolated from controlled studies of limited duration or result from analysis of a limited number of explanted devices. These are usually explanted due to infection or trauma at the site, or failure of the device or an unrelated death of the patient (Chawla et al., "Degradation in polyurethane pacemakers leads," 12th Annual Meeting of the Society for Biomaterials, Minneapolis-St. Paul, Minn., 1986). Unfortunately, data collected in this manner do not constitute well-controlled studies.

Approaches to validating the in vivo performance life time of materials and devices include analyses of the interface between the host and the material of the device. Much of this is aimed at determining the biocompatibility of the material with blood or blood components and also with assessing the toxicity of leachables from the material. Increasingly, discussion is starting to focus on measurement of material degradation after implantation. Biological model systems and methods of monitoring and predicting the degradation are needed for each type of material and site of use of the devices, as the host response will vary with these two parameters.

Some of the properties of materials that are reflective of their performance potential have been studied: surface characterization as hydrophobic or hydrophilic by measurement of the contact angle, crystallinity of the material, lipophilic nature, (Fulghum et al., "Surface characterization," *Anal. Chem.,* 61, pp. 243R-269R, 1989; Ratner et al., "Biomaterial surfaces," *J. of Biomedical Materials Research: Applied Biomaterials,* 21 (A1), pp.59-90, 1987; National Heart, Lung and Blood Institute Working Group Guidelines for Blood-Biomaterial Interactions, 1985), mineralization (Stokes et al., "Environmental stress cracking in implanted polyurethanes," 2nd World Congress on Biomaterials, Wash., DC, 1984) and thrombogenicity (Schoen, F. J.: Interventional and Surgical Cardiovascular Pathology: Clinical Correlations and Basic Principles, W. B. Saunders, Philadelphia, 1989, pp. 1-415), and phase transition (Wilkes and Emerson, *J. Applied Physics,* 47:4261, 1976).

At present there is very little routine testing performed to determine the effect of the host response on the device and it's materials. An understanding of the interaction between these materials and the body's environment is fundamental to the prediction of long term functional performance. This is due to the fact that the nature of the environment is difficult to determine and duplicate in vitro.

The research literature shows that all materials elicit a reaction from the human body. This reaction is purposeful: to attack, destroy and remove the invading device. There are several chemical mechanisms of degradation for a material in the bioenvironment. These include: mineralization, specifically calcification (Hennig et al., "Calcification of artificial heart valves and artificial hearts," *Proc. Eur. Soc. Artificial Organs,* 8, pp. 76-80, 1981), hydrolysis including enzymatic hydrolysis (Ratner et al., "In vitro studies of the enzymatic biodegradation of polyetherurethanes," Abstract: 12th Annual Meeting of the Society for Biomaterials, Minneapolis-St. Paul, Minn., 1986; Chu et al., "The effect of gamma irradiation on the enzymatic degradation of polyglycolic acid absorbable sutures," *J. Biomedical Materials Res.,* 17, pp. 1029-1040, 1983; Smith et al., "The enzymatic degradation of polymers in vitro," *J. Biomedical Materials Res.,* 21, pp. 991-1003, 1987; Williams, "Some observations on the role of cellular enzymes in the in vivo degradation of polymers," *Corrosion and Degradation of Implant Materials.* ASTM, ASTM Special Technical Publication 684, B. C. Syrett and Acharya, Eds. Philadelphia, pp. 61-75, 1978), and/or oxidation. These processes when coupled with a static or dynamic mechanical stress induced, for example, by implant fixation technique or motion, result in structural changes in the material as in the case of polyurethane insulated pacemaker leads (Stokes et al., 1984). This would manifest itself as a cracked or crazed surface and results in the loss of insulating properties of the polyurethane. Knowledge of the role of enzymes, of other biochemical compounds and of cells in inducing such mechanisms is important in devising means for protecting materials during long term implantation. Since many polymeric implant materials have molecular sites which can be oxidized, this may be a principle means of degradation.

The initial response to an invasive device is described as the inflammatory reaction with subsequent wound healing (Marchant et al., "Biocompatibility and an enhanced acute inflammatory phase model," *Corrosion and Degradation of Implant Materials: Second Symposium.* ASTM STP 859, A. C. Fraker and C. D. Griffin, Eds., ASTM, Philadelphia, pp. 251-266, 1985; Marchant et al., "in vivo biocompatibility studies, VII, Inflammatory response to polyethylene and to a cytotoxic polyvinylchloride," *Journal of Biomedical Materials Research:* 20, pp. 37-50, 1986). One of the first systems activated in the inflammatory reaction is the complement cascade. Recent evidence indicates that the clotting mechanism or complement cascade can be modulated by the type of material employed (Kiyosawa et al., "Effects of Intraocular Lens Materials on Complement Activation and Macrophage Function, Nippon Ganka Gakkai Zasshi; 92(4), pp. 603-610, 1988) These results are interpreted to mean that there are specific sites or chemical groups on certain materials that cause activation of parts of the complement pathway. Certain materials such as silk sutures and nylon fibers suppress the complement cascade (Zimmerli et al., "Pathogenesis of Foreign Body Infection: Description and Characteristics of an Animal Model," *Journal of Infectious Diseases,* 146(4), pp. 487-497, 1982; Zimmerli et al., "Comparative Superoxide-Generating System of Granulocytes from Blood and Peritoneal Exudates," *Infection and Immunity.* 46(3), pp. 625-630, 1984; Zimmerli et al., "Pathogenesis of Foreign Body Infection: Evidence for a Local Granulocyte Defect," *Journal of Clinical Investigation,* 73, pp. 1191-1200, 1984). There is the possibility that complement results in an oscillatory reaction which continually attracts the leucocytes to the implant site. Analyses which demonstrate this phenomenon could be very useful in the prediction of material performance in the host.

The primary cells attracted during the initial phase of the inflammatory response are the polymorphonuclear leucocytes with their secretions of lysozymes and hydrolytic and oxidative enzymes and oxidative oxygen products such as hydrogen peroxide, superoxide anion hydroxyl radical, and hypochlorous acid (Allen, "Phagocytic leukocyte Oxygenation Activities and Chemiluminescence: A Kinetic Approach to Analysis," In: Methods in Enzymology: Bioluminescence and Chemiluminescence, Part B, Volume 133, Marlene A. DeLuca and William D. McElroy, Eds., Academic Press, Inc., New York., pp. 449-493, 1986; Thompson et al., "Oxygen metabolism of the HL-60 cell line: Comparison of the effects of monocytoid and neutrophilic differentiation," *J. Leukocyte Biology.* 43, pp. 140-147, 1988; Cohen et al., "Phagocytes, O-2 reduction and hydroxyl radical," *Reviews of Infectious Diseases,* 10(6), pp. 1088-1096, 1988). This arsenal of chemicals can effect the material and eventually degrade it to the point of malfunction. Subsequent to this acute response, macrophages are differentiated and attracted to the site, via cytokines and lymphokines, where they too attempt to destroy the foreign material. Adaptive processes have evolved to enable both cell types to engulf by phagocytosis particulate invaders such as microorganisms and to destroy them by secretion of energetic, metabolic oxidative products and enzymes within the phagosome. Concomitant with this response is the utilization of increased amounts of metabolic oxygen, referred to as the respiratory burst (LKB Wallac, "The LKB Wallac 1251 luminometer—A Tool for the detection of opsonophagocytic dysfunctions," *Product News: Luminescence Analysis.* pp. 1-6, 1985). Although it is thought that the oxidative oxygen products are primarily responsible for killing of intracellular parasites, it is known that these macrophages can still kill organisms such as trophozoites without the utilization of additional oxygen-using mechanisms. Such non-oxidative microbiocidal functions are currently under investigation by a number of researchers, i.e., the study of defensins (Elsbach and Weiss, "Chapter 24: Phagocytic Cells: Oxygen-independent antimicrobial systems." In: Inflammation: Basic Principles and Clinical Correlates. John I. Gallin, Ira M. Goldstein and Ralph Snyderman, 1988).

When the material is too large for engulfment, the macrophage enlarges into a multinucleated cell, termed a foreign body giant cell. This process is termed "frustrated phagocytosis" (Ziats et al., "In vitro and in vivo Interactions of Cells with Biomaterials," *Biomaterials.* 9, pp. 5-13, 1988), since the macrophages cannot actually engulf the very large invader, in this case the material of the implant. These cells attach to the material and may cause damage due to extracellular secretions. This chronic phase may continue for extended periods. The subsequent formation of a fibrous capsule around the device results in a "walling-off" or exclusion of the device from the biological milieu. In order to study the biological response without this exclusion and be able to sample by aspiration, cellular populations at the site, researchers in this area have used a stainless steel cage to hold the implant materials to be tested (Marchant et al., "In vivo biocompatibility studies, I, The cage implant system and a biodegradable hydrogel," *Journal of Biomedical Materials Research,* 17, pp. 301-325, 1983; Marchant et al., "Preliminary cell adhesion and surface characterization studies," *Journal of Biomedical Materials Research.* 18, pp. 309-315, 1984; Marchant et al., "In vivo biocompatibility studies, V, In vivo leukocyte interactions with Biomer," *Journal of Biomedical Materials Research.* 18, pp. 1169-1190, 1984; Marchant et al., 1986). These studies produced much information on cellular aspects of the inflammatory reaction. Studies with biomedical materials have shown changes in the cellular supernatant secretions that contain fibroblastic and thymocyte proliferative Interleukin-1-like activity (Miller et al., "Characterization of biomedical polymer-adherent macrophages: Interleukin 1 generation and scanning electron microscopy studies," *Biomaterials,* 10, pp. 187-196, 1989; Miller et al., "Human monocyte/macrophage activation and interleukin 1 generation by biomedical polymers," *Journal of Biomed. Mater. Res.* 22, pp. 713-731, 1988; Miller et al., "Generation of IL1-like activity in response to biomedical polymer implants: A comparison of in vitro and in vivo models," *J. Biomed. Res.,* 23, pp. 1007-1026, 1989). Zimmerli et al. (1982, 1984) have used cages composed of teflon and of PMMA to minimize the inflammatory response to the test holder of the material.

Conventional biocompatability tests measure cell death, cell damage, mutagenicity or other cytopathology at the site of implantation into test animals or tissue culture vessels. These measures do not distinguish among the various cell responses and are subjectively quantified, at best. Knowledge of the amount and rate of production of oxidative products in response to different materials is desirable since it could serve as an indicator of a material's stability in the biological environment and could be useful in predicting the long term reliability of the material. Biological oxidizing agents include: $H_2O_2$, $O_2^-$, OH or HOCL (Castranova et al., Chapter 1: "Chemiluminescence from Macrophages and Monocytes. Cellular chemiluminescence," In: Cellular Chemiluminescence, Volume II, Knox Van Dyke and Vincent Castranova, Eds. CRC Press, Boca Raton, Fla., pp. 3-19, 1987; Allen, 1986; Lilius et al., "Chemiluminescence emission from enriched fraction of human natural killer cells," *Analytical Applications of Bioluminescence and Chemiluminescence.* L. J. Kricka, P. E. Stanley, G. H. G. Thorpe and T. P. Whitehead, Eds., Academic Press, New York, pp. 397-400, 1984; Lilus et al., "A very sensitive and rapid chemiluminescence method for the measurement of phagocytosis," *Analytical Applications of Bioluminescence and Chemiluminescence,* L. J. Kricka, P. E. Stanley, G. H. G. Thorpe and T. P. Whitehead, Eds., Academic Press, Inc., New York, pp. 401-404, 1984). It is therefore desired to be able to continuously monitor the production of some of these oxidants with a real time non-destructive method. Conventional technology may attempt to use chemical or spectrophotometric assays to determine the amount of oxidative products instantaneously produced in response to introduction of a material in the biological environment. However, the short lifetime of the oxidative product and the fact that they are continuously produced by the cells introduces errors into these methods. In some cases, the presence of the opaque biomaterial interferes with the assay and removing the test cells from the material is difficult and not quantitative. The cells are thus perturbed and the subsequent measures fail to be true to the original biological conditions.

SUMMARY OF THE INVENTION

Therefore, it is an object of the present invention to provide a method for continuously monitoring in real time the generation of oxidative products from cell-material interactions in vitro.

It is a further object of the present invention to provide a method for determining the amount of oxidative products as a result of activation of biological cells, which provides an indication of the degree of the inflammatory response and influences the degree of acceptance of a biomaterial introduced into a biological environment.

Another object of the present invention is to provide a method for assessing the toxicity of any material or extract thereof on a cell type that produces oxidative products.

Still a further object of the present invention is to provide a method for determining of some aspects of biocompatability of any material with any cell type that produces oxidative products.

Yet another object of the present invention is to provide a method to determine the modulation of some aspects of the isolated cell immune response by monitoring the chemiluminescence response caused by cell-biomaterial interaction.

Yet a further object of the present invention is to provide a method to determine the degree of suppression or enhancement of the phagocytosis response caused by cell-biomaterial interaction in vitro as an indication of a suppression/enhancement of the immune response.

Yet still a further object of the present invention is to provide a chemiluminescence method for assessing the microbiocidal response of phagocytic cells.

It is yet a further object of the present invention to provide a chemiluminescence method for monitoring tumor cell killing.

It is still a further object of the present invention to provide a method for detecting the effects of leachables from materials on the host cells.

Still a further object of the present invention is to provide a chemiluminescence method to investigate material surface effects on host cells such as effects from using smooth or rough surfaced materials.

Still yet another object of the present invention is to provide a method to investigate material surface effects on host cells caused by manufacturing processing conditions as well as effects on in vitro cells from bioresorbable materials and their breakdown products.

The foregoing objects and others are accomplished in accordance with the present invention, generally speaking, by providing a method for analyzing in real time in vitro interaction between cells and materials which comprises introducing cells and material into an environment for interaction; monitoring over real time chemiluminescent light produced by oxidative products produced by said cells; and determining the amount of said oxidative products produced over real time based on the chemiluminescence measurements.

Further scope of the applicability of the present invention will become apparent from the detailed description and drawings provided below. However, it should be understood that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is further illustrated in the accompanying drawings wherein.

Figure 8:
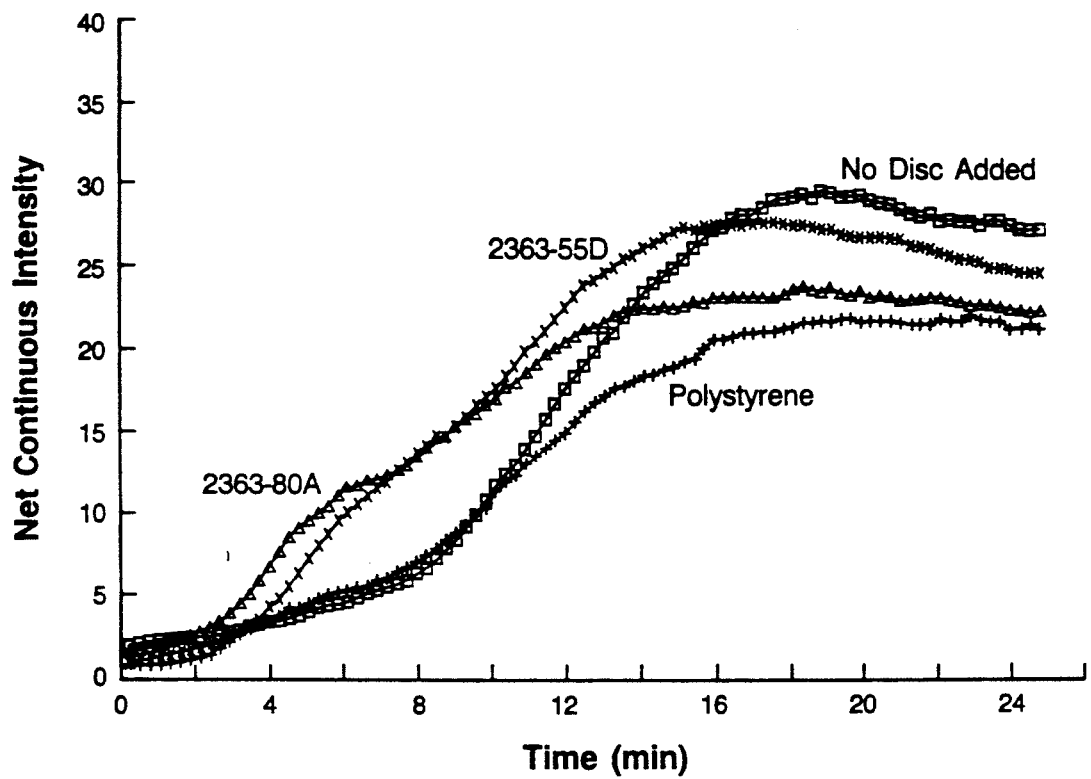
Figure 9:
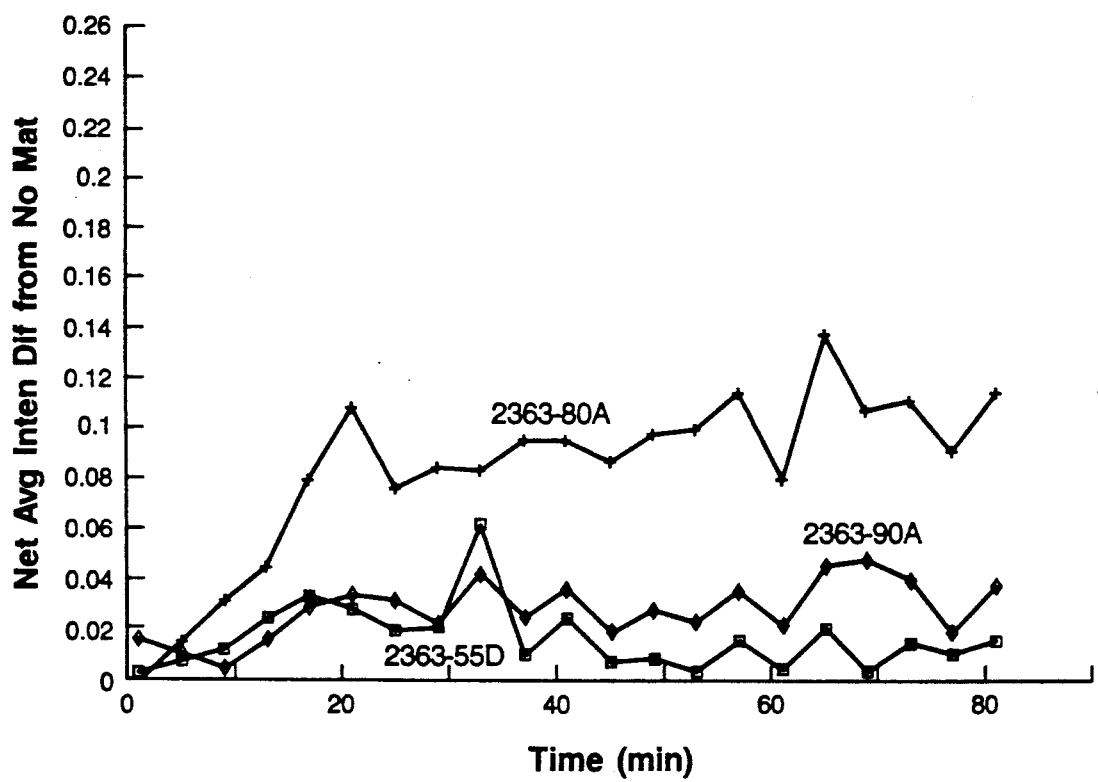
Figure 10:
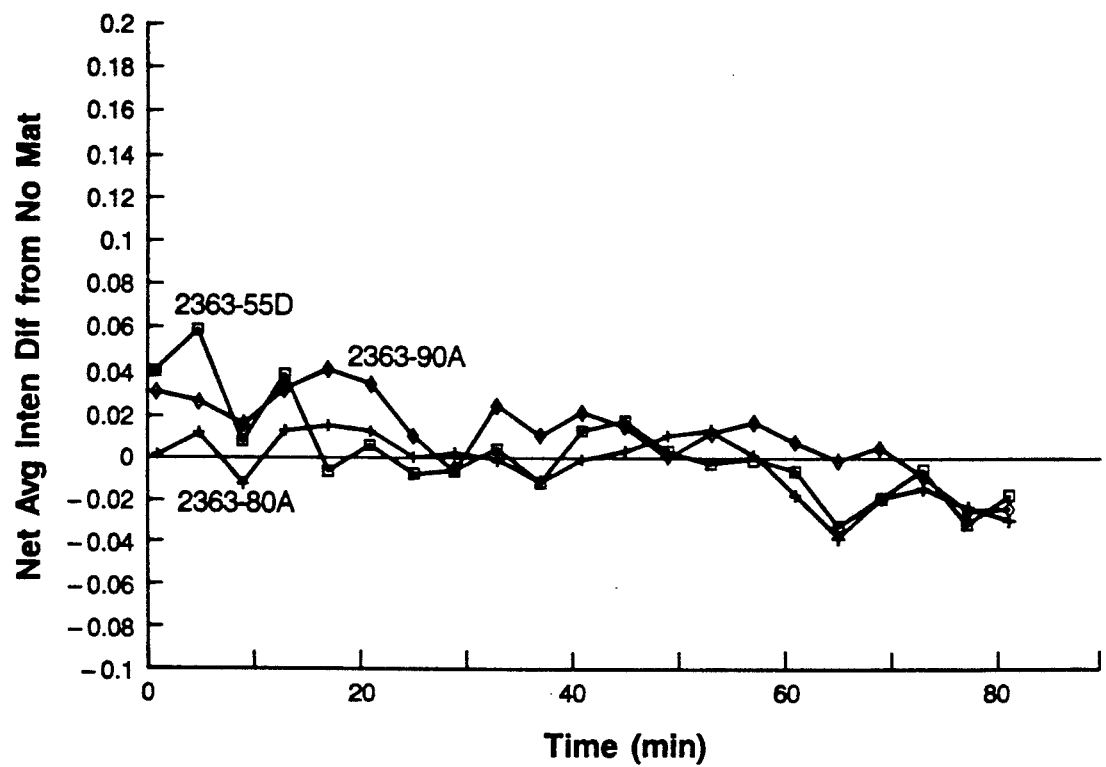

versus Time (min.) in the presence of D3 differentiated HL-60 cells and OZ stimulus;

FIG. 8 shows the net continuous intensity in the presence of OZ when the D3 HL-60 cells are incubated with Pellethane 2363−80.A, −55D, polystyrene or no disc; and FIG. 9 is a graph of the continuous net average intensity of no material difference versus Time (min.) for 2363−80A, −55D and −90A for lucigenin with diluted whole blood; and FIG. 10 is a graph of the continuous net average intensity of no material difference versus Time (min) for 2363−80A, −55D and −90A for luminol with diluted whole blood. with diluted whole blood.

DETAILED DESCRIPTION OF THE INVENTION

The present invention relates to a real time, non-destructive method for continuously monitoring the production of oxidative products by measuring the chemiluminescent light produced by the oxidative products generated as a result of exposure of cells to a material. The material may be a biomaterial proposed for implantation. A non-exhaustive list of materials which may be employed in accordance with the present invention includes metals, ceramics, bioresorbables, breakdown products of bioresorbables, hydroxyapatite, polyglycolic acids, nylon, silk, polymers, polylactic acids, glutaraldehyde and otherwise fixed naturally occurring materials.

Polymorphonuclear leucocytes (PMN) and macrophages produce a low amplitude light during phagocytosis (Allen, 1986, Miles et al., "Chemiluminescence associated with phagocytosis of foreign particles in rabbit alveolar macrophages," *Life Sciences*, 20, pp. 165–170, 1977). Lymphocytes do not have the respiratory burst and do not produce light. The light, in some cases, is due to the production of hydrogen peroxide or superoxide (Allen, 1986) and the subsequent oxidation of some substrate, perhaps the engulfed microorganism.

The mechanism of light production is complicated and not yet fully understood. Microorganisms, a particulate stimulus such as opsonized zymosan, or the material of an implant are detected on the cell membrane through a receptor. Once attached to the receptor, several events occur which include depolarization of the cell membrane and activation of several key enzymes inside the cell. The most important of these enzymes is protein kinase c, which in conjuction with ATP, phosphorylates proteins within the cell and activates NADPH oxidase, which is membrane-bound. The phagocytized particles are walled off by an invagination of the cell membrane, into a vacuole. The phagocytic vacuole then fuses with the lysosome to form a phagolysosome which has an internal pH of approximately 4.8. In the phagolysosome, NADPH oxidase in the presence of $O_2$ generates superoxide ($O_2^-$). Through the action of superoxide dismutase (SOD), $O_2^-$ is dismutated to hydrogen peroxide ($H_2O_2$) $H_2O_2$ serves as the substrate for myeloperoxidase (MPO) which in the presence of $Cl^-$ breaks down $H_2O_2$ via the following reaction to hypochlorous acid (HOCL):

$$H_2O_2 + Cl^- = H_2O + HOCL$$

HOCL is believed to be the key factor responsible for microbiocidal action (Allen, 1986). Hydroxyl radical, which is also implicated in microbiocidal action is generated through the Haber-Weiss reaction where in the presence of $Fe^{++}$:

$$H^+O_2 + H_2O_2 = OH + H_2O + O_2$$

$$\cdot OH + H_2O_2 = H_2O + O_2^- + H^+.$$

Chemiluminescent probes (CLP) such as luminol which primarily detects hydrogen peroxide and lucigenin which primarily detects superoxide, enhance the native light production. Luminol produces light via the following dioxygenation reaction:

$$Luminol + H_2O_2 = aminophthalate + N_2 + hv \sim$$

This reaction can be initiated by the production of $H_2O_2$ by activated PMN's or macrophages. When luminol is oxidized by hydrogen peroxide, a factor of $10^4$ increase in light production results above the native $H_2O_2$ light production (Allen, 1986; Lilius et al., 1986). In fact, further enhancement of the light by an additional factor of 10 can be achieved by the use of hypochlorous acid with luminol (Seitz, "Chemiluminescence from the reaction between hypochlorite and luminol," *J. of Physical Chemistry*. 79(2), pp. 101–106, 1975; Isacsson and Wettermark, "The determination of inorganic chlorine compounds by chemiluminescence reactions," *Analytica Chimica Acta*, 83, pp. 227–239, 1976). Lucigenin produces light by a reductive dioxygenation and also enhances the native superoxide light production.

This light can be measured with either a scintillation counter used in a non-coincidence mode or with other sensitive photometric instrumentation such as a luminometer. Alternatively, in situ monitoring with a microscope photometer or fiber optic sensor to measure the light while the cells are attached to the material, will provide real-time determinations of the hydrogen peroxide or superoxide produced.

Thus a multiple monitor of oxidative oxygen products could be envisioned which provides direct measurements for each of these products using light detection.

The chemiluminescence method for continuously monitoring in real time the generation of oxidative products from in-vitro cell-biomaterial interactions of the present invention can be performed with cell lines such as Human Leukemic cells (HL-60) which have been differentiated into PMN-like or Monocyte/Macrophage-like cells; tumor cell line hybridomas; Cell types deficient in the respiratory burst such as Chronic Granulomatous Disease cells or a mouse macrophage cell Line IC21 as controls; Monocytic cell lines; Primary Human cells such as platelets, monocytes, pmns, fibroblasts, endothelial cells; whole blood and isolated blood cells. Cell types would be selected according to the purpose of the investigation. The technique is not limited to the above mentioned primary and continuous cell systems, but can be used with any cells that produce oxidative products.

Leucocyte phagocytosis is considered to result from their activation. Monitoring of their response to biomaterials could be performed by developing a quantitative phagocytosis indicator. This can be done by measuring the modulation of the phagocytic response of the cells to opsonized zymosan or other phagocytosable particles in the presence of CLPs and materials. The degree of cellular activation by the material will influence the rate of phagocytosis and thus the light production. If the oxidative products are not available to the soluble CLPs in the surrounding medium, an analysis of the intraphagolysosomal oxidative products can be made by feeding the cells beads that have the CLPs bound to them. When the phagocyte is "turned on" by the material, it will phagocytize or engulf particles. If the particles contain bound luminol or lucigenin, these CLPs will be oxidized by the hydrogen peroxide or superoxide anion secreted into the phagosome and light will be emitted. The light will be proportional to the amount of reactive oxygen secreted and thus indicate in real time the concentration of oxidant available to degrade the material. Uchida and Hosaka ("Direct measurement of phagosomal reactive oxygen by microsphere-bound luminol," *Macrophage Biology, pp.* 545–550, 1985) have developed luminol labelled beads for use in feeding assays to quantitate the concentration of hydrogen peroxide released during phagocytosis. Luminol and lucigenin labelled beads are currently commercially available from Polysciences, Inc. (Warrington, Pa.).

Comparisons can be made between the hydrogen peroxide or superoxide anion secreted within the phagosome and that produced extracellularly by also measuring the light from luminol or lucigenin, respectively, that is added to the extracellular milieu. In this manner, the source of the oxidation can be monitored.

As a correlative measure of phagocytic activity, particles containing fluorescent dyes could be exposed to phagocyte cultures in the presence of different biomaterials substrates. Measurement of the level of cellular fluorescence would then provide an indicator of the number of particles which have been engulfed by the individual phagocytes and, therefore, a measure of their phagocytic activity. This is performed by feeding experiments in which the phagocytic cells are first allowed to take up the labelled particle and then the excess beads are washed from the cells. The individual cells are imaged using a microscope-photometer equipped for fluorescence excitation and the specific emission of the beads phagocytized within the cells is measured. Alternatively, the fluorescence intensity of the beads which have been phagocytized could be measured in a fluorometer after solubilizing the cellular material to release the internalized beads. Phagocytic activity can also be measured using confocal scanning fluorescence microscopy using image analysis and the counting of the beads (Hook et al, "Confocal scanning fluorescence microscopy: A new method for phagocytosis research," *J. Leukocyte biology,* 45, pp. 277–282, 1989).

At least two types of CLP particles may be used: FITC-labelled latex beads of about 5 micron diameter and Uranyl-doped glass beads of 2-20 micron diameter (Uchida et al., 1985; Sano et al, "Phagocytosis of Microspheres by Polymorphonuclear Leukocytes," The Third World Biomaterials Congress, Kyoto, Japan, Abstract 5B1-11, 1988). The glass beads are supplied by Dr. Michael Epstein, National Institutes of Standards and Technology, and do not fade during excitation. The latex beads are supplied by Flow Cytometer Systems, Inc. and show an exponential decay during excitation. It is impractical to attempt a labelling of the glass beads with FITC since it is an organic molecule which would be unstable at the temperatures required to fabricate the glass beads. It is known that the glass matrix stabilizes the fluorophore (uranyl oxide) during excitation (Kaplan and Picciolo, "Characterization of Instrumentation and Calibrators for Quantitative Microfluorometry for Immunofluorescence Tests," *J. of Clinical Microbiology,* 27(3), pp. 442–447, 1989).

PREFERRED EMBODIMENTS

Materials and Methods

Instrumentation

Figure 1:
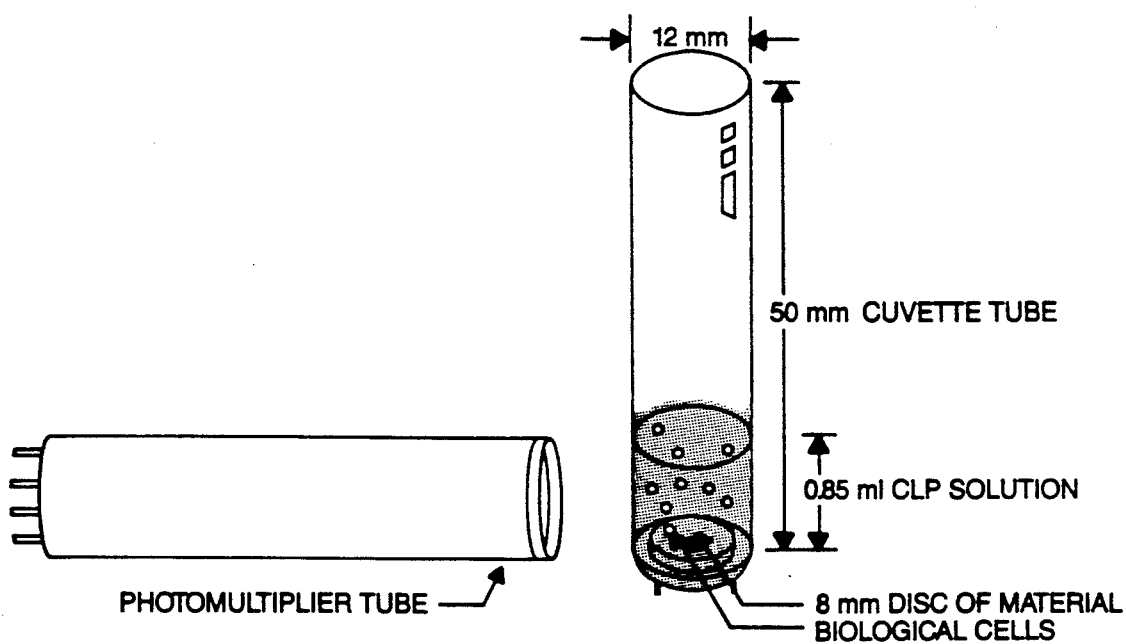
FIG. 1 is a schematic drawing for the LKB WALLAC 1251 Luminometer showing the relationship between the photomultiplier tube, a disc of material inside a cuvette with a solution of chemiluminescence probe (CLP), and cells in a holding medium used in accordance with one embodiment of the method of the present invention.

LKB WALLAC 1251 Luminometer. The luminometer has been previously described (Lilius et al, 1984b; LKB, 1985). A total volume of 0.85 ml of reagents was added to the luminometer cuvettes. This volume filled the cuvette up to a scored line on the cuvette which is the optimal focus for the photomultiplier tube as illustrated in FIG. 1 which shows the relationship between the photomultiplier tube, a disc of material inside a cuvette with a solution of chemiluminescence probe (CLP), and cells in a holding medium. Background noise associated with self luminescence can be reduced by keeping vials and reagents in the dark before measurement. The cuvettes were placed in the 25 chamber carousel in the LKB-WALLAC 1251 luminometer, set to 37° C. It is important that the reaction be run at 37° C. in order for the reaction kinetics to simulate the in vivo conditions. When measuring multiple specimens, sampling was set to measure 25 samples every 4 minutes for 15 seconds at a time using the Phagocytosis Program 1251/SOO-15 version 1.1. Output data was analyzed either or both by the Phagocytosis Program or imported into a Lotus 1-2-3 spreadsheet for data manipulation, graphics and statistics. Other photometric instrumentation can be used including a liquid scintillation counter set in the "out-of-coincidence" mode.

Measurement Calibration. A standard radioactive scintillation source produced by New England Nuclear Corp., or luminol in a scintillator standard, referred to as ALMS, provided by Dr. Robert Allen is used as a calibration for the light measurements and a hydrogen peroxide concentration curve as a conversion from the measured voltage to concentrations of cellular-produced hydrogen peroxide. When interference from the other reagents used or efficiency of light measurements is changed by the disc of material, a recovery % is measured by measuring the intensity produced by adding a high level of $H_2O_2$ to the spent cuvette. Mathematical corrections for this recovery % is made to each intensity measurement.

Biomaterials

Samples of biomaterials were punched into 8 mm discs approximately 1.5 mm thick. The thickness was determined by the source of the material. The Polystyrene was punched from a Corning tissue culture flask (Corning, Inc., Corning, N.Y.). The Polyethylene was the NIH NHLBI-DTB Reference Material from Applied Biomedical Corp. (Abiomed) Danvers, Mass. The Polyurethanes were Pellethane 2363−80A, 2363−90A and 2363−55D from Dow Chemical, Corp. (Midland, Mich.) in sheets. The Pyrolytic Carbon was prepared as 7 mm discs by Carbomedics, Inc. (Austin, Tex.). All discs were cleaned by sonication in pyrogen-free deionized water and air-dried in a Biological Safety Cabinet.

The samples were sterilized by ethylene oxide (12% ethylene oxide in 88% freon, aerated for 12 h), with the exception of the Pyrolytic Carbon which was sterilized by flaming in 70% ethanol. Alternatively, the pyrolytic carbon is sonicated in 70% ethanol, air dried in a Biological Safety Cabinet and used or sterilized With ethylene oxide.

Reagent Preparation

Holding Media

The HM consists of 25 mM Hepes, 5.5 mM glucose, 5 mM KCl, 145 mM NaCl, 1 mM $CaCl_2$ and 0.1% Porcine skin gelatin (300 Boom, Sigma Chemical Co., Inc., St. Louis, Mo.) The glucose acts as an energy source necessary for the cells to produce the respiratory burst and is essentially the same as described by Allen (1986). The gelatin is a source of protein, stabilizes the cells and retards the adherence to surfaces, such as glass (Yanai et al., "Chemiluminescence by Polymorphonuclear Leukocytes Adhering to Surfaces," *Infection and Immunity*, 32(3) pp. 1181-1186, 1981). The medium is osmotically balanced and the pH maintained at 7.4. The main advantage of this medium is that it stabilizes the CL reaction and enhances the reproducibility of the results. This medium has been used with the HL-60 cells.

Hydrogen Peroxide. A stock solution of $6 \times 10^{-2}$M $H_2O_2$: (Sigma Chemical Company, St. Louis, Mo.) was prepared daily in 25 mM Hepes buffer, pH 7.3. Subsequently, serial twofold dilutions to $1.17 \times 10^{-4}$M $H_2O_2$ were made to inject into the luminometer cuvettes. These concentrations are the final concentration in the luminometer cuvette containing 0.85 ml total volume reagents.

CLPs and CL Triggers. The CLPs and CL triggers were prepared by essentially the same methods described by Allen (1986). All reagents were obtained from Aldrich, Milwaukee, Wis., unless specified otherwise.

Luminol. Stock solution of 10 mM luminol in 0.05M sodium tetraborate decahydrate (Borax), pH 9.0 was prepared. This solution was diluted in 25 mM HEPES buffer, pH 7.3 to achieve a working dilution of $5.6 \times 10^{-4}$M.

Lucigenin. A $5 \times 10^{-3}$M Lucigenin stock solution in pH 7.3 Dulbecco's Phosphate Buffered Saline was prepared.

PMA (Phorbol-12-myristate-13-acetate). A stock solution of 1 mg/ml was prepared in HPLC grade DMSO using Polysciences, Inc., (Warrington, Pa.) PMA. A working solution of 0.1 mg/ml was prepared by making a 1:10 dilution of the stock in pH 7.3 Dulbecco's PBS.

Concanavalin A (Con A). A 20 mg/ml stock solution in pH 7.3 Holding Media (without gelatin) was prepared.

In some of the examples below, the following reagents supplied by Dr. Robert Allen of Stephen's Enterprises, Little Rock, Ark. were used: Blood Diluting Medium (BDM), Luminol Complete Medium (LCM), Lucigenin Complete Medium (DCM) and opsonized zymosan (OZ). These reagents were prepared according to the methods described by Dr. Allen in 1986.

Source and Maintenance of Cells

Mouse Cell Cultures. Initially, two cell types were used to demonstrate the feasibility of the chemiluminescence approach. Mouse macrophage (P388D1) from American Type Culture, Rockville, Md., ATCC No. TiB63, originally from alveolar aspirage, have been cultured in RPMI 1640 or DMEM medium with 10% fetal bovine serum and subcultured twice weekly. They were grown at 37 C with 7% CO2. A second cell line of mouse macrophage, IC21, was obtained from Dr. James, George Washington University, Washington, D.C. and maintained in Iscoves complete medium with 10% fetal bovine serum. This strain is known to be missing the "respiratory burst" which accompanies the activities of phagocytosis (Scott et al. "The respiratory burst is not required for killing of intracellular and extracellular parasites by a lymphokine-activated macrophage cell line," *Eur. J. Immunol.*, 15, pp. 553-558 1985).

Fresh, Whole Human Blood

Fresh blood from a human volunteer was drawn into a $K_3$-EDTA tube by venipuncture. The blood was gently mixed on a Adams Nutator rotator. The first 1:100 dilution was performed by adding 0.1 ml of the blood to 9.9 ml of BDM or HM (see the CL Procedures section below). The final dilution was made by adding 0.1 ml of diluted blood to 0.65 ml of either LCM or DCM to a cuvette for the LKB-WALLAC 1251 Luminometer. Luminol and lucigenin solutions (see CL Procedures section) could be substituted in place of LCM or DCM. The blood was stored at 14° C.

Human Cells Lines. The Human Promyelocytic leukemic cell line (HL-60) was obtained from ATCC (ATCC No. CCL 240). These cells were cultured in RPMI 1640 medium with 10% fetal bovine serum at 37° C. with 5% $CO_2$ and subcultured twice weekly. HL-60 cells can be differentiated into PMN-like cells (using hypoxanthine or retinoic acid) or into macrophage-like cells (using vitamin $D_3$).

Differentiation of HL-60 Cells

Retinoic Acid (RA). (Aldrich Chemical Company, Milwaukee, Wis.). A $1 \times 10^{-3}$M stock solution in 100 percent ethanol was prepared. 50 ul of stock RA was added per 50 ml culture media ($1 \times 10^5$ cells/ml) to differentiate the HL-60 cells. The cells were incubated for 5 days to 37° C. with 5% $CO_2$ to allow maximal differentiation.

Hypoxanthine (Hx). (Aldrich Chemical Company, Milwaukee, Wis.). A 2 mM stock solution was prepared in pH 7.3 Dulbecco's PBS. The HL-60 cells ($1 \times 10^5$ cells/ml) were incubated in the presence of 0.2 mM Hx (final concentration) at 37° C. with 5% CO, for 5 days to allow optimal differentiation to PMN-like cells.

1,25-dihydroxycholecalciferol (Vitamin $D_3$). $D_3$ was obtained from Dr. Milan Uskokovic, Hoffman-LaRoche, Inc., Nutley, N.J. A $5.03 \times 10^{-4}$M stock solution in 100 percent ethanol was prepared. The HL-60 cells were differentiated into macrophage-like cells in $1 \times 10^{-6}$M $D_3$ (final concentration) by adding 0.1 ml stock $D_3$ to 50 ml media ($1 \times 10^5$ cells/ml). The cells were incubated for 4 days at 37° C. with 5% $CO_2$. A second dose of 0.1 ml $D_3$ was given on day 2 after addition of the differentiating agent.

Dislodging and Processing Differentiated HL-60 Cells

Hx- and RA-differentiated cells. Hx and Ra-differentiated cells do not firmly adhere to the polystyrene growth flask. The cells are dislodged by pipetting the medium in the flask up and down several times. The medium containing the cells is centrifuged for 3 min at 800 rpm at 14° C. and resuspended in HM at a final cell concentration of $1 \times 10^5$ cells/ml.

Vitamin $D_3$-differentiated Cells. The spent medium containing non-adherent cells is pipetted off from the flask. 10 ml HM is added to the flask and the flask is rotated to wet the entire growth surface of the flask. The flask is placed on ice for 5 min. and the cells are dislodged by repeatedly, sharply hitting the side of the flask. The HM is pipetted off and the procedure is repeated for another 5 min. icing; the HM from each of the icing steps are pooled. The pooled HM containing the dislodged cells is centrifuged at 800 rpm for 3 min at 14° C. and the pellet is resuspended in HM to a final concentration of $1 \times 10^5$ cells/ml. The % viability and total cell count is determined with Trypan Blue exclusion using a Hemocytometer.

Controls

Negative controls. HM or BDM without added luminol or $H_2O_2$; HM or BDM without luminol, but with $H_2O_2$ added; LCM without $H_2O_2$ added. Another negative control utilized is heat-killed HL-60 cells. The HL-60 cells are heat-killed by heating the cells up to 65° C. for 3 min. in a heating block. The heat-killed cells are useful negative controls since they do not produce chemiluminescence.

RESULTS $H_2O_2$ concentration curve and instrument linearity. Luminol complete media was diluted with blood diluting media to give a concentration of 48.67 uM luminol. An aliquot of 0.1 ml from each tube of serially diluted hydrogen peroxide was added to 0.75 ml of diluted luminol (43.1 uM, final luminol concentration in cuvette). The CLP's as well as the HM could also be used in this experiment.

Figure 2:
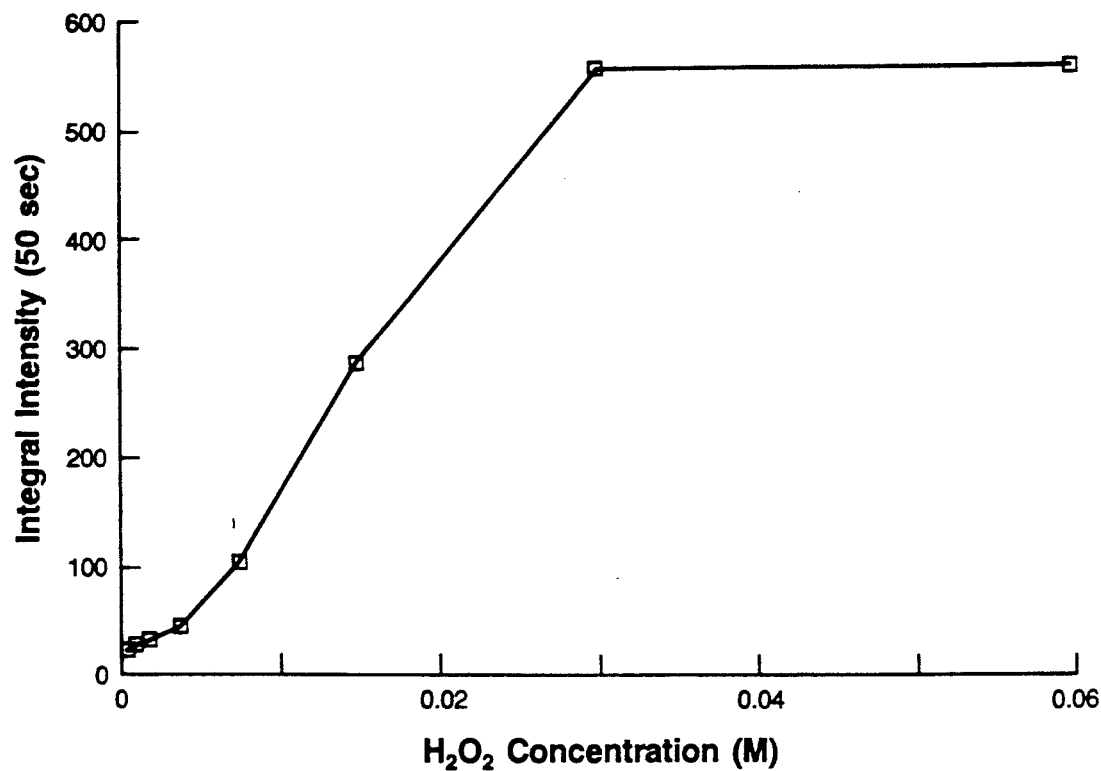
FIG. 2 is a graph of $H_2O_2$ concentration versus integral intensity.

The concentration curve is linear from 0.03M to 1.9 uM $H_2O_2$. As is shown in FIG. 2 which is a graph of $H_2O_2$ concentration versus integral intensity, the highest concentration of hydrogen peroxide ($5.98 \times 10^{-2}$M) used showed saturation. The correlation coefficients for the linear regression for the concentration range $2.99 \times 10^{-2}$M to $3.7 \times 10^{-3}$M are 0.9981 and 0.9962, respectively, for mean and integral. These data, along with the calibration standards validate the linearity of the instrument response and the reagents in the desired concentration range.

Recovery. In order to determine whether the physical presence of the material disc would interfere with the light measurement, a recovery test was performed using a range of hydrogen peroxide concentrations buffered in 25 mM HEPES at pH 7.4. The linear range of sensitivity of the hydrogen peroxide concentrations was determined to be between $10^{-3}$ and $10^{-5}$M. Three dilutions of hydrogen peroxide within this range were injected into cuvettes containing 8 mm discs of the various materials. The reproducibility was 10%. The ratio between the light intensity at each dilution of hydrogen peroxide when there was no disc (control) added and that with the disc present showed values close to one (range from 1.1 to 0.9) with no statistically significant differences among the materials. Thus we concluded that the presence of material discs in the sample cuvette does not significantly effect the efficiency of the light signal reaching the photomultiplier tube.

Figure 3:
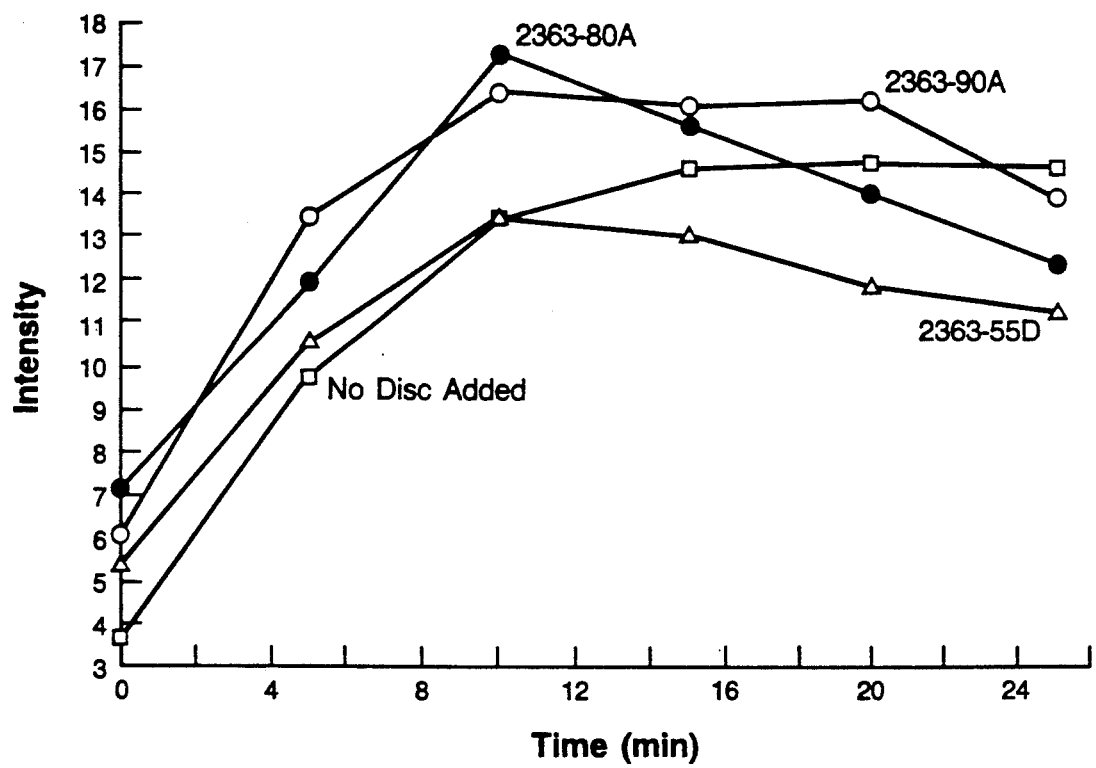
FIG. 3 is a graph of light intensity over time for mouse macrophage cell line P388.
Figure 4:
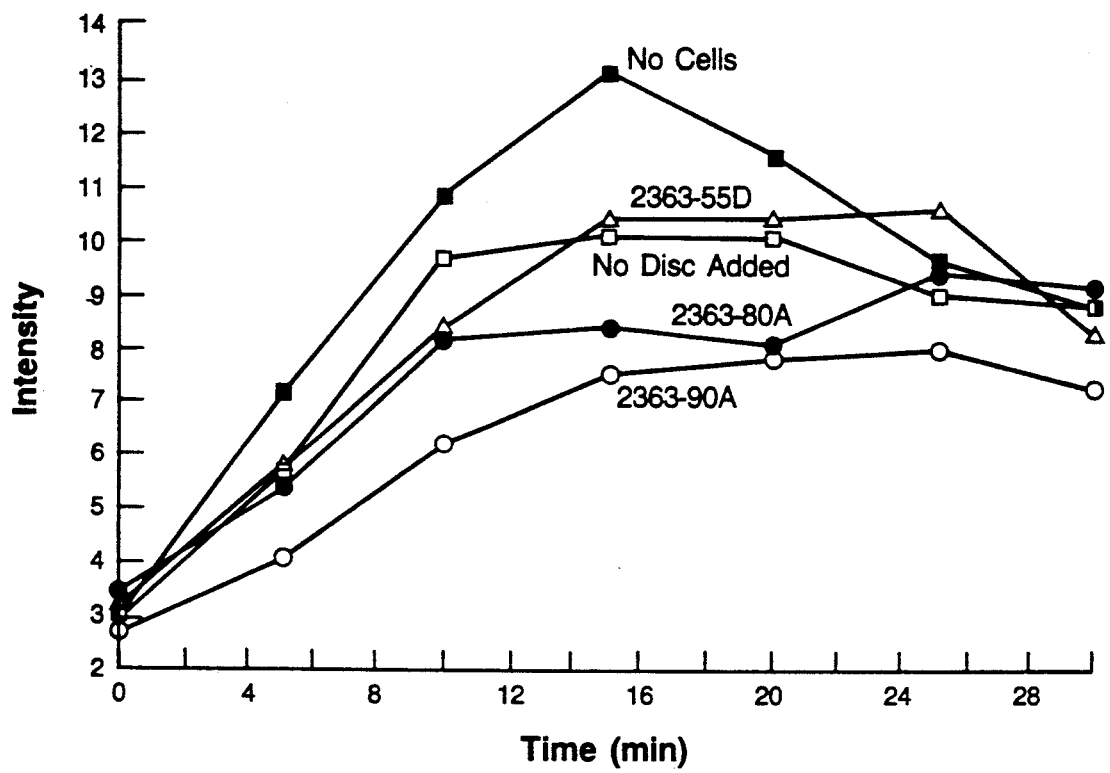
FIG. 4 is a graph of light intensity over time for mouse macrophage cell line IC21.

Mouse Macrophage Cell Cultures. A continuous monitor of the intensity from mouse macrophages was performed by adding the CLP, luminol, to cuvettes containing cells and discs of several materials. The time course of light intensity is shown in FIG. 3 for P388 and FIG. 4 for IC21 after pretreatment with three types of polyurethane: Pellethane 2363-80A (-●-), -90A (-O-) and -55D (-△-). Note that (-□-) represents a sample with no disc and, in FIG. 4, (-■-) represents a sample with no cells. The macrophages which had not undergone any pretreatment and the reagents without any macrophages are also shown. Hydrogen peroxide was added to all tubes in this experiment. Omitting the pre-treatment with the material, showed a typical reaction. The addition of the macrophages perturbed the light production differently depending on the pretreatment received. Macrophages that had been pretreated with the softer polyurethanes −80A or −90A gave increased light intensities when measured over time than those that were pretreated with the harder polyurethane −55D. This is true for the macrophage strain known to have the "respiratory burst". The IC21 showed no statistically different change in the amount of light compared with the untreated or the sample with no cells added, indicating that the respiratory burst correlates with the cells' response to the materials. These results have demonstrated a correlation with the response of the cells to the type of material or something that leaches out of the material. Pretreatment with different types of material influences the amount and rate of light production. In addition, the light production rate is also seen to be influenced by the strain of macrophage used.

Figure 5:
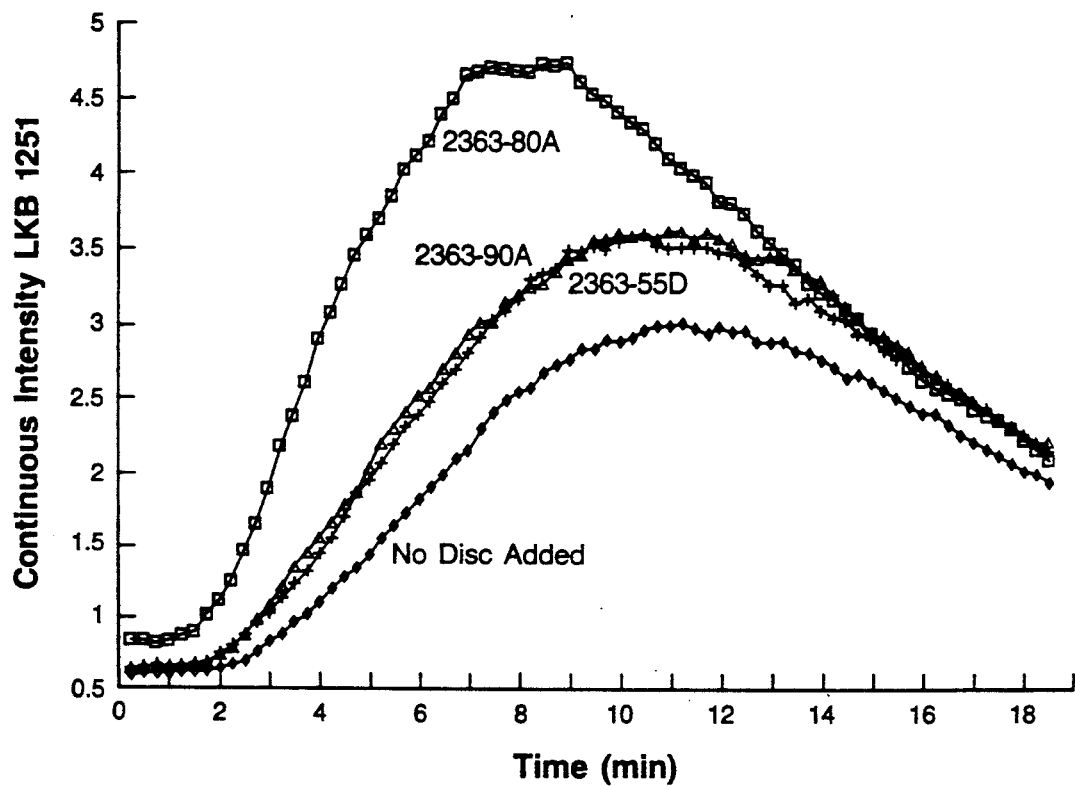
FIG. 5 is a graph of continuous intensity versus time in minutes for each of the sample cuvettes in the presence of hypoxanthine-differentiated HL-60 cells and the stimulus Con A.

Chemiluminescence Reaction of Hypoxanthine-Differentiated HL-60 Cells in the Presence of a Soluble Stimulus. 0.75 ml of hypoxanthine differentiated HL-60 cells (final cell concentration in cuvette $1 \times 10^6$ cells/ml) were added to the LKB-WALLAC 1251 luminometer cuvettes containing an 8 mm disc of either Pellethane 2363-80A, −90A, −55D or no added disc (control). The materials had previously been cleaned and sterilized as described above. Hypoxanthine differentiates the HL-60 cells into polymorphonuclear leucocyte-like cells. 100 ul of HM containing $5.6 \times 10^{-4}$ luminol ($5.6 \times 10^{-5}$M final concentration in cuvette), 1 mM $CaCl_2$ and 0.02 mg/ml Con A was added to each cuvette to initiate the chemiluminescence reaction. FIG. 5 is a graph of continuous intensity on the LKB-WALLAC 1251 vs time in minutes for each of the sample cuvettes. Pellethane 2363-80A (-□-) showed the greatest material response after approximately 6-9 minutes. The Pellethane 2363-90A (-△-) and 2363-55D (+) showed a lower material response than the 80A, but the response was still elevated above the no disc control. The −90A, −55D and no disc (-◊-) cuvettes reached the peak intensity at a slightly later time than the −80A (10-12 minutes). The experiment was repeated with the same batch of hypoxanthine differentiated cells and the data were averaged with the corresponding data in the first run of the experiment and shown in Table 1.

TABLE 1

Effect of Polyurethanes on the Intensity from Hypoxanthine differentiated HL-60 cells. Results are the average from two runs with two samples of each material in each run over a 20 minute time course.

| Intensity over 20 min. | No Disc | 80A | 90A | 55D |
|---|---|---|---|---|
| SUM | 146.38 | 158.47 | 148.08 | 126.31 |
| PEAK | 2.87 | 3.42 | 2.94 | 2.67 |
| AVG. | 2.50 | 2.29 | 2.03 | 1.83 |

Figure 6:
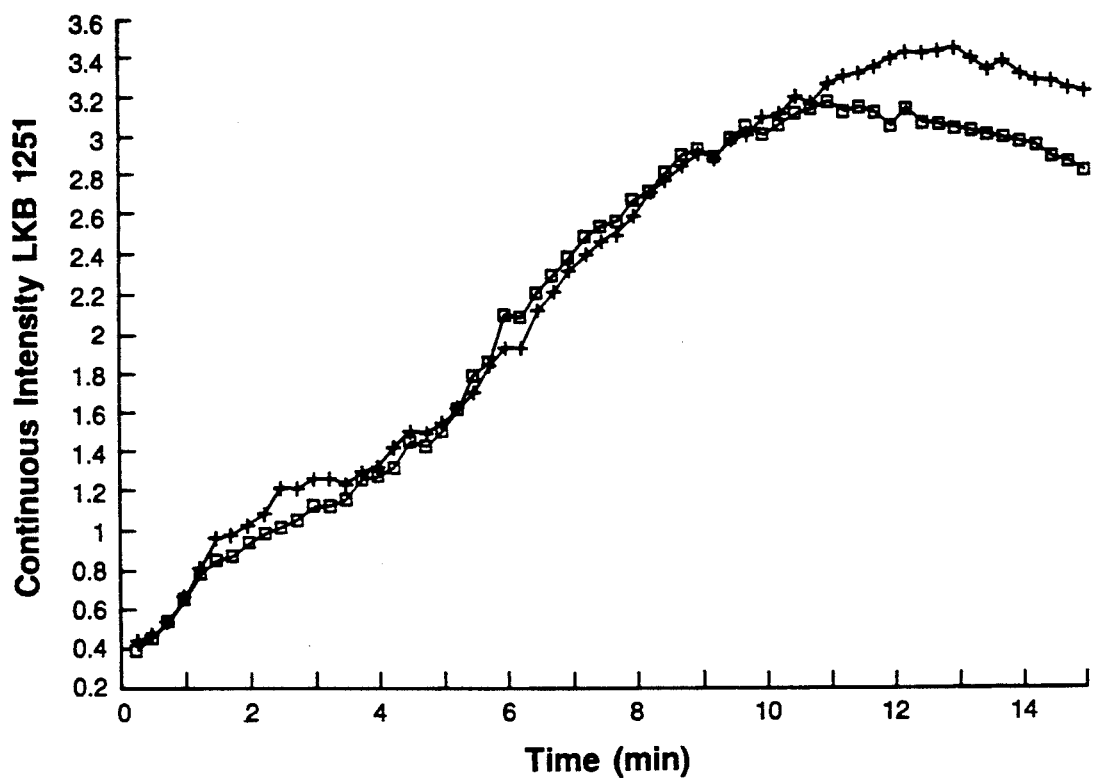
FIG. 6 is a graph of continuous intensity versus time in minutes to show the reproducibility of the materials effects assay.

The data shows a small inhibition by 2363-55D from the no material. The 2363-80A gave the highest intensity. There does not appear to be differences in the order of the material effect, whether the Sum, Peak or Mean intensity is analyzed. When two cuvettes were run on 2363-80A (-□- and +), the results were plotted in FIG. 6 which is a graph of continuous intensity versus time in minutes to show the reproducibility of the materials effects assay.

Chemiluminescence Reaction of Vitamin $D_3$-Differentiated HL-60 Cells in the Presence of a particulate Stimulus. 0.75 ml of vitamin $D_3$-differentiated HL-60 cells in LCM (final cell concentration in cuvette $1 \times 10^5$ cells/ml) were added to the LKB-WALLAC 1251 luminometer cuvettes containing discs of either Pellethane 2363-80A, or −55D, polyethylene, polystyrene, pyrolytic carbon or no disc (control). The materials had previously been cleaned and sterilized as described above. Vitamin $D_3$ differentiates the HL-60 cells into macrophage-like cells. OZ was added to each cuvette to initiate the chemiluminescence reaction.

Figure 7:
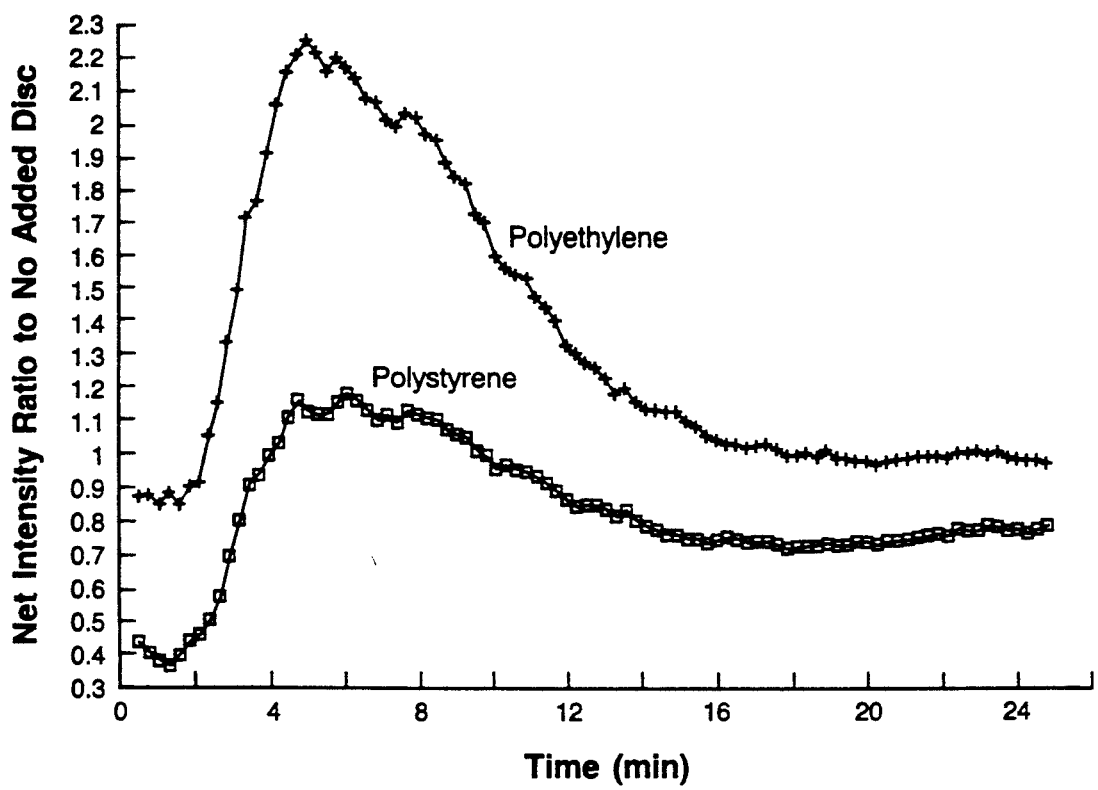
FIG. 7 is a graph showing the ratio of the net intensity of the cells in the presence of two materials to the net intensity of the cuvette with no added disc (control)

FIG. 7 shows the ratio of the net intensity of the cells in the presence of a material to the net intensity of the cuvette with no added disc (control). If the cells in the presence of the materials were equal to the no disc control, then the ratio would be one. Polyethylene (+) elicited 2.3 times the light intensity than that from polystyrene (-□-) at 4–8 min. after adding the stimulus. This data indicates that the polyethylene enhances the phagocytosis of the opsonized zymosan. FIG. 8 shows the net continuous intensity in the presence of OZ when the cells are incubated with Pellethane 2363-80A (-△-), −55D (×), polystyrene (+) or no disc (-□-). At 4–6 minutes after adding the OZ, the curve is inflecting upward for 2363-80A, −55D. However, the curve is deflecting downward at 6–8 min for the polystyrene and no disc cuvettes.

Diluted Whole Blood Cells. Two chemiluminescent probes (luminol and lucigenin) were used to continuously monitor oxidative product concentration in real time with several polymer materials in the presence of whole, fresh human blood. Samples of each material were run in duplicate and the experiment was repeated once on the next day using the prior day's sample of blood which had been kept at 14° C.

The discs of materials were added to polystyrene LKB-WALLAC 1251 cuvettes and 0.75 ml of the diluted blood in LCM or DCM added. Luminol, lucigenin, and HM could also be substituted in the experiment. An empty tube containing either ALMS or the New England Nuclear light standard was run with each experiment.

Diluted blood was measured with discs of polyurethanes for 84 minutes and the results plotted for lucigenin in FIG. 9 and for luminol in FIG. 10. The continuous net average intensity from luminol difference from the no disc measurement showed small differences from 55D (-□-) and 90A (-◇-). These data showed oscillations which may indicate that hydrogen peroxide is being competitively consumed in the reaction cuvette by other constituents of the blood, such as catalase. The lucigenin results showed a higher intensity above the no disc measurement with the 90A or 55D indicating some stimulation of the production of superoxide. The 80A (+) polyurethane showed greater intensity increasing up to 20 minutes then maintaining its amplitude above the other polyurethanes. This may be caused by some additive leaching from the softer polyurethanes with time of exposure of the cells to the disc.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for analyzing in real time in vitro interactions between biological cells and biomaterial proposed for implantation which comprises:
   introducing biological cells and biomaterial proposed for implantation into an environment for interaction, wherein said environment includes chemiluminescent probes which emit chemiluminescent light in the presence of oxidative products produced by said cells;
   monitoring over real time the amount of chemiluminescent light produced by oxidative products of said cells in the presence of said biomaterial as a first measurement;
   introducing a biological activator into said environment, wherein said biological activator causes the production of oxidative products;
   monitoring over real time the amount of chemiluminescent light produced by oxidative products of said cells as a second measurement;
   repeating the above steps under the same conditions except without the introduction of said biomaterial; and
   measuring the amount of said oxidative products produced by the interaction between said biological cells and said biomaterial in said environment over real time based on a comparison of each of the first chemiluminescence measurements, respectively, and each of the second chemiluminescence measurements, respectively.

2. The method as defined in claim 1, wherein said oxidative products comprise hydrogen peroxide, superoxide, or combinations thereof.

3. The method as defined in claim 2, wherein said cells are selected from the group of cell lines consisting of Human Leukemic cells (HL-60), tumor cell line hybridomas, cells lacking the respiratory burst, Chromic Granulomatous Disease cells, Monocytic cell lines, Primary Human cells, whole blood cells, and isolated blood cells.

4. The method as defined in claim 3, wherein said chemiluminescent probes comprise particles which contain bound luminol or lucigenin.

5. The method as defined in claim 4, wherein said chemiluminescent light is monitored using a photometric instrument selected from the group consisting of a luminometer, a scintillation counter, a microscope photometer and a fiber optic sensor.

6. The method as defined in claim 5, wherein said biomaterial is selected from the group consisting of polyethylene, polyurethane and pyrolytic carbon.

7. The method as defined in claim 5, wherein said biomaterial is selected from the group consisting of metals, ceramics, bioresorbables, breakdown products of bioresorbables, hydroxyapatite, polyglycolic acids, nylon, silk, polymers, olyactic acids, glutaraldehyde and fixed naturally occurring materials.

8. The method as defined in claim 1, wherein said biological cells are selected from the group of cell lines consisting of Human Leukemic cells (HL-60), tumor cell line hybridomas, cells lacking the respiratory burst, Chromic Granulomatous Disease cells, Monocytic cell lines, Primary Human cells, whole blood cells, and isolated blood cells.

9. The method as defined in claim 8, wherein said Primary Human cells are selected from the group consisting of monocytes, polymorphonuclear leukocytes, fibroblasts and endothelial cells.

10. The method as defined in claim 1, which further comprises assessing biodegradation characteristics and biocompatability characteristics of said biomaterial by correlating the produced amount of said oxidative products with the measured characteristics of said material.

11. The method as defined in claim 1, which further comprises measuring the inflammatory reaction or the relative toxicity caused by said biomaterial by determining the produced amount of said oxidative products.

12. The method as defined in claim 1, which further comprises measuring suppression or enhancement of the phagocytosis response of the biological cells caused by the interaction between said cells and said biomaterial as an indication of a suppression or enhancement of the cell immune response by said material.

13. The method as defined in claim 1, which further comprises monitoring tumor cell killing in the presence of said material.

14. The method as defined in claim 1, which further comprise measuring the effects of leachables from said biomaterial on said biological cells.

15. The method as defined in claim 1, wherein said chemiluminescent probes comprise particles which contain bound luminol and lucigenin.

16. The method as defined in claim 15, wherein said particles comprise latex or glass beads.

17. The method as defined in claim 1, wherein said chemiluminescent light is monitored using a photometric instrument selected from the group consisting of a luminometer, a scintillation counter, a microscope photometer and a fiber optic sensor.

18. The method as defined in claim 1, wherein said biomaterial is selected from the group consisting of polyethylene, polyurethane and pyrolytic carbon.

19. The method as defined in claim 1, wherein said biomaterial is selected from the group consisting of metals, ceramics, bioresorbables, breakdown products of bioresorbables, hydroxyapatite, polyglycolic acids, nylon, silk, polymers, polylactic acids, glutaraldehyde and fixed naturally occurring materials.

20. The method as defined in claim 1, wherein said biological activator is selected from the group consisting of opsonized zymosan, phorbol-12-myristate-13-acetate and concanavalin A.

21. The method as defined in claim 1, wherein said chemiluminescent probes comprise luminol or lucigenin in solution.

* * * * *